US006171585B1

(12) United States Patent
Jordan et al.

(10) Patent No.: US 6,171,585 B1
(45) Date of Patent: *Jan. 9, 2001

(54) IVIG IMMUNOSUPPRESSION IN HLA-SENSITIZED TRANSPLANT RECIPIENTS

(75) Inventors: Stanley C. Jordan, Manhattan Beach; Dolly B. Tyan, Los Angeles, both of CA (US)

(73) Assignee: Cedars-Sinai Medical Center, Los Angeles, CA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/312,521

(22) Filed: Sep. 26, 1994

Related U.S. Application Data

(63) Continuation of application No. 08/061,719, filed on May 14, 1993, now abandoned.

(51) Int. Cl.[7] ................... A61K 39/395; C07K 16/00; C07K 16/18; C07K 16/42
(52) U.S. Cl. ..................... 424/130.1; 424/131.1; 530/387.1; 530/387.2; 530/389.1
(58) Field of Search .............. 424/131.1, 130.1; 530/389.1, 388.1, 387.2

(56) References Cited

U.S. PATENT DOCUMENTS

| 5,200,400 | 4/1993 | Teramoto et al. . |
| 5,204,329 | 4/1993 | Ackerman et al. . |

OTHER PUBLICATIONS

Peraldi et al., Transplantation, 1996, 62(11):1670.*
Riggio, R.R., et al., "Enhanced Kidney Graft Survival With Retroplacental Source γ–Globulin," *Transplantation*, 23(6):636–641 (1982).
Auch N Cross in Transplantation Immunology CD. Bach and Auchin Cross, Wiley–Liss NY 1995 pp. 211–218.*
1. Tyan et al. Transplantation 57: 553–562 (1994).*
2. Riggio et al. Proc. Eur. Dial. Transplant. Assoc. 16:426 (1979).*
Harris et al. TIBTECH, 11:42, 1993, Therapeutic. . . Age.*
Sullivan et al., N. Eng. J. Med., 323:705, 1990, Immunomodulation. . . transplantation.*

Clark et al., The Experimental Foundations of Modern Immunology, 1991, pp. 420–443.*
Rodey et al., Transplantation, 1989, 48 (1): 54–57.*
Buckley and Schiff, "The Use of Intravenous Immune Globulin in Immunodeficiency Diseases," *The New England Journal of Medicine* 325:110–117 (1991).
Dwyer, "Manipulating the Immune System with Immune Globulin," *The New England Journal of Medicine* 326:107–116 (1992).
Glotz, et al., Inhibition of Anti–HLA Antibodies (Ab) Cytotoxicity and Synthesis by Intravenous Polyclonal Immunoglobulins (IVIg), ASN Abstracts, Abstract No. 87P (1992).
Jordan and Tyan, "Intravenous Gamma Globulin (IVIG) Inhibits Lymphocytotoxic Antibody Activity in Vitro," Proceedings of the 24th Annual Meeting of The American Society of Nephrology (1991).
Kaveri et al., "Intravenous Immunoglobulins IVIg in the Treatment of Autoimmune Diseases," *Clin. Exp. Immunol.* 86:192–198 (1991).
Lambrechts et al., "Mechanism of Allograft Tolerance in Nonhuman Primates: Purification of a Specific Isotype of IgG With Suppressor Activity," *Transplantation Proceedings* 25:329–330 (1993).
The National Institute of Child Health and Human Development Intravenous Immunoglobulin Study Group, "Intravenous Immune Globulin for the Prevention of Bacterial Infections in Children with Symptomatic Human Immunodeficiency Virus Infection," *The New England Journal of Medicine* 325:73–80 (1991).
Stiehm, "New Uses for Intravenous Immune Globulin," *The New England Journal of Medicine* 325:123–125 (1991).
Sullivan et al., "Immunomodulatory and Antimicrobial Efficacy of Intravenous Immunoglobulin in Bone Marrow Transplantation" *The New England Journal of Medicine* 323:705–712 (1990).
Yadin et al., "Intravenous Immunoglobulin (IVIg) Reduces Antibody Responses in Highly Sensitized Dialysis Patients," ASN Abstracts, Abstract No. 87 (1992).

* cited by examiner

*Primary Examiner*—Phillip Gambel
(74) *Attorney, Agent, or Firm*—Campbell & Flores

(57) ABSTRACT

Methods are provided for transplanting a histoincompatible organ allograft in a subject, methods for enhancing organ allograft survival in a subject, methods for reducing the amount of anti-HLA alloantibodies in a transplant candidate and methods to make candidate less susceptible to rejection.

18 Claims, 2 Drawing Sheets

IVIG IMMUNOSUPPRESSION IN HLA-SENSITIZED TRANSPLANT RECIPIENTS

This application is a continuation of application Ser. No. 08/061,719, now abandoned, filed May 14, 1993.

The present invention relates to methods of transplantation. In a particular aspect, the invention relates to methods to immunosuppress a potential transplant recipient so as to be amenable to transplant with donor organs obtained from a variety of donors including histoincompatible donors. In another aspect, the present invention relates to methods to reduce the likelihood of rejection of a transplanted organ by a transplant recipient. In yet another aspect, the invention relates to methods to prolong the survival of a transplant recipient. In a further aspect, the invention relates to methods of transplantation which reduce the extensive immunosuppressive treatment post-transplantation.

BACKGROUND OF THE INVENTION

Although transplantation of organs is becoming commonplace, rejection of the donated organ by the patient remains a serious problem. Except for cases of organ donation between identical twins or the special instance of transplantation in individuals with severe combined immunodeficiency disease, all transplant recipients currently require an immunosuppressive regimen to prevent rejection. Although these immunosuppressive drugs are administered post-transplantation in an attempt to prevent rejection, they also suppress the body's defenses against infection. Thus, transplantation requires a continued effort to induce acceptance of the graft without paralyzing the body's immune system.

Various regimens in use employ one or more of the following agents or therapies: (1) corticosteroids, such as prednisone; (2) cytotoxic drugs, such as azathioprine and cyclophosphamide; (3) x-ray irradiation therapy; (4) antilymphocyte and anti-thymocyte globulins; (5) cyclosporine; and (6) monoclonal antibodies such as OKT3, which reacts specifically with the CD3 antigen-recognition structure of human T cells and blocks the T cell effector function involved in allograft rejection.

All of the above described therapy methods are administered post-transplant and have undesirable side effects. For example, corticosteroids may cause decreased resistance to infection, painful arthritis, osteoporosis, and cataracts. Cytotoxic agents may cause anemia and thrombocytopenia, and sometimes hepatitis. The antilymphocyte globulins may cause fever, hypotension, diarrhea, or sterile meningitis. Cyclosporine may cause decreased renal function, hypertension, tremor, anorexia, and elevated low-density lipoprotein levels. OKT3 may cause chills and fever, nausea, vomiting, diarrhea, rash, headache, photophobia, and occasional episodes of life-threatening acute pulmonary edema.

There are two types of allograft rejection, acute humoral rejection (hyperacute rejection) and acute cellular rejection (acute rejection). Hyperacute humoral rejection is generally an overwhelming, irreversible process that occurs when organs are transplanted into recipients who have preformed cytotoxic antibodies against antigens of the donor allograft, such as anti-HLA antibodies (i.e., immunohistoincompatibility). Up until now, no combination of immunosuppressive drugs has been capable of reversing or inhibiting this rapid hyperacute rejection process.

Intravenous gammaglobulin (IVIg) has been in use since 1981, primarily for prophylaxis in those with primary or secondary immunodeficiency states. Beneficial results have also been reported in the treatment of childhood idiopathic thrombocytopenic purpura, in CMV prophylaxis for bone marrow transplantation, amelioration of GVHD (graft versus host disease), and other autoimmune disorders. IVIg is known to contain antiidiotypic antibody activity against a number of autoantibodies (i.e., anti-ANA and anti-ANCA), but little is known about IVIg's antiidiotypic activity against alloantibodies. IVIg is known to block antibody response in vivo and in vitro although the exact mechanisms are not known. IVIg has been used successfully to obtain improved post transfusion platelet increments in refractory patients.

A wide source of donor organs are potentially available to various patients in need of a transplant. However, due to positive crossmatch that is typically observed between a highly sensitized organ-recipient and organ-donor, only a very small percentage of available donor-organs are actually suitable for transplant for any given potential organ-recipient. Thus, methods useful for increasing the percentage of donor-organs available to organ-recipient candidates are needed.

BRIEF DESCRIPTION OF THE INVENTION

In accordance with the present invention, we have discovered that candidate transplant patients can be treated prior to transplantation so as to improve the likelihood of successful transplantation. The improvement is accomplished by increasing the likelihood of a negative crossmatch between the transplant recipient and the specific organ-donor. Thus, methods for transplanting an allograft in a patient are provided. Particularly, the present invention provides a method for preventing hyperacute rejection of a transplanted organ or tissue by a recipient mammal that includes the step of administering to a mammal, prior to the transplantation, an anti-HLA-antibody-depleting agent.

The invention methods are useful to expand the available source of donor organs which are acceptable for a given transplant recipient. The invention methods permit a highly sensitized or HLA sensitized patient to be successfully immunosuppressed in vivo and subsequently transplanted with a crossmatch negative, but histoincompatible, donor-organ. The present invention improves the prognosis of a transplant recipient for long-term survival ("actuarial graft survival"), and reduces the need for immunosuppressive treatment. The present invention prevents infection and does not add to the patient's immunosuppressive load, e.g., does not increase the risk of malignancy or infection. In addition, the invention method reduces the time that potential transplant candidates spend waiting for a compatible, crossmatch negative donor.

An pre-transplant assay for predicting which patients are amenable to treatment with the invention methods of transplantation is also provided. The pre-transplant assay also allows the determination of one or more residual anti-HLA antibody specificities remaining in the transplant candidate, which thus permits the determination and avoidance of a specifically defined population of donor-organs at transplant.

DETAILED DESCRIPTION OF THE INVENTION

Figures 1A, 1B, 1C:
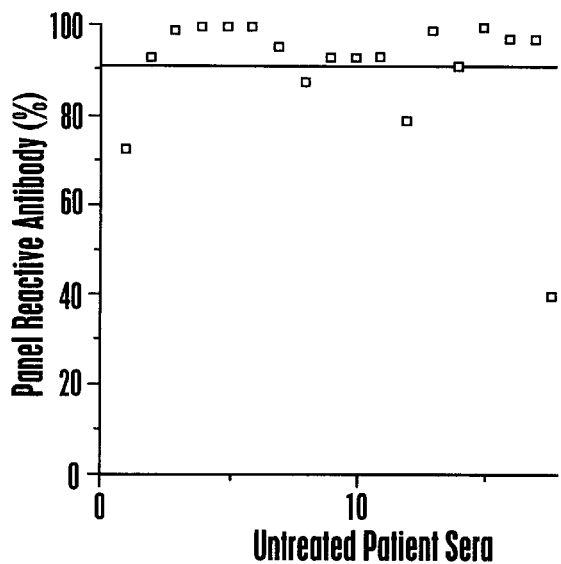
FIGS. 1A–1C shows sera from 18 highly sensitized patients tested for cytotoxic panel reactive antibody (PRA) to HLA on a 50 cell panel. Sera were untreated (1A), diluted 1:2 with glycine (1B), or diluted 1:2 with IVIg, 10% (1C). Horizontal bars indicate the mean PRA in each group.

In accordance with the present invention, there is provided a method for transplanting an allograft in a patient, said method comprising:
  administering to said patient, prior to transplantation, an effective amount of an anti-HLA-antibody-depleting-agent suitable to substantially reduce the level of anti-HLA antibodies, and thereafter
  transplanting said allograft.

It has been found that IVIg treatment of highly sensitized individuals reduces the level of anti-HLA antibodies in their serum and is therefore useful for inhibiting the rejection of an allograft. An advantage of the invention method is the fact that a wider source of donor organs are made available. The need for immunosuppressive treatment after transplantation is somewhat reduced. In addition, the "actuarial graft survival" rate is increased to a greater extent than in transplant recipients who are not treated according to the invention method.

Rejection of organ allografts is caused by a variety of factors, such as, for example, the anti-donor mediated humoral antibody response. In this mode of graft rejection, allograft rejection is directly related to the presence of specific anti-HLA antibodies directed against the HLA antigen of the donor in the sera of the organ-recipient. The higher the concentration of anti-HLA antibodies directed against the HLA antigen of the donor in the sera, the higher the level of allograft rejection, thus producing a shorter actuarial allograft survival time. For example, if the organ-recipient has a strong anti-HLA antibody directed against the HLA antigen of the donor, then rejection of an allograft may be immediate. As a means to determine the presence of these potential donor antibodies, the higher the PRA, the more likely the recipient is to have antibody to many antigens (i.e., many donors).

As used herein, the phrase "prior to transplantation," when used in the context of administering the anti-HLA-antibody-depleting-agent, refers to the commencement of treatment of the patient according to the invention method before the occurrence of the actual transplantation procedure. The length of time before the transplantation procedure is not critical, so long as sufficient time is allowed for a substantial reduction in the level of anti-HLA antibodies to occur. For example, suitable time periods prior to transplantation are as long as a few years, preferably 2 years, to as short as a few days. Preferred time periods prior to transplantation are about 1 week to about 6 months with 2 weeks to about 6 weeks being more preferred. Preferably, the substantial reduction in the level of anti-HLA antibodies will also occur prior to transplantation. In one embodiment of the present invention, the continued application of the anti-HLA-antibody-depleting agent post-transplantation is contemplated, as needed.

The term "anti-HLA-antibody-depleting-agent" refers to a composition that is able to inhibit the activity of one or all of the anti-HLA alloantibody specificities in the serum of a given individual. The inhibition may occur by physically blocking the physiological activity of the anti-HLA antibodies or may occur by downregulating the production of anti-HLA antibodies. Suitable anti-HLA-antibody-depleting-agents contemplated for use in the practice of the present invention include IVIg, the IgG-fraction of IVIg, anti-idiotypic anti-HLA antibodies, and the like. Presently preferred are IVIg and the IgG-fraction of IVIg prepared as described in Example 5.

Intravenous immunoglobulins (IVIg) are therapeutic preparations of normal polyspecific IgG obtained from plasma pools of over 6,000 healthy blood donors. Currently used preparations are made of intact IgG with a distribution of subclasses corresponding to that of normal serum and have a half-life of three weeks in vivo for IgG1, IgG2 and IgG4, and somewhat less for IgG3. Most of the preparations contain only traces of IgA, IgM and of Fc-dependent IgG aggregates [see Kaveri et al., in Clin. Exp. Immunol. 86:192–198 (1991)]. IVIg contain up to 30% of F(ab')$_2$—F(ab')$_2$ dimers as assessed by size-exclusion chromatography and electronmicroscopy. The dimers are the consequence of V-region complementarity between immunoglobulins in the pool [see Roux & Tankersley, in J. Immunol. 134:1387 (1990)]. Owing to the large number of donors, IVIg represent a wide spectrum of the expressed normal human IgG repertoire, including antibodies to external antigens, autoreactive antibodies and anti-antibodies.

Commercial IVIg preparations are widely available, for example, from Cutter Laboratories, Baxter, Sandoz, MedImmune, and Venoglobulin. The commercial IVIg preparations typically contain 5–20% IVIg in maltose or glycine carriers. Also contemplated for use herein are aqueous solutions containing higher concentrations of IVIg, such as approximately 25%–75%. Substantially pure preparations of the "IgG-fraction of IVIg" are also suitable for use herein. Substantially pure IgG-fractions typically contain greater than 50% of an IgG-fraction, preferably greater than 75%, and most preferably greater than 90% of an IgG-fraction.

Other anti-HLA-antibody-depleting-agents contemplated for use herein include anti-idiotypic anti-HLA antibody preparations. Suitable anti-idiotypic anti-HLA antibodies are either polyclonal or monoclonal. Methods of preparing antibodies are well known in the art. See, for example, Benoit et al., in Proc. Natl. Acad. Sci. USA Vol. 79:917–921 (1987).

A typical anti-HLA antibody population in a patient contains a variety of anti-HLA alloantibody specificities that each recognize a distinct HLA antigen. These specificities (subclasses) are well-known in the art, e.g., "anti-HLA-A1", "anti-HLA-A2", "anti-HLA-B8", "anti-HLA-B51", and the like. In a preferred embodiment of the invention transplant method, the entire population of anti-HLA-antibody subclasses is reduced (i.e., PRA=0).

In another embodiment of the present invention, the reduction in anti-HLA-alloantibodies does not include the reduction of every subclass, e.g., "anti-HLA-A1", "anti-HLA-A2", "anti-HLA-B8", and/or "anti-HLA-B51." Where the reduction in anti-HLA antibodies does not include all subclasses, the reduction is sufficient to allow the remaining subclasses to be determined. This allows the pool of potential organ-donors to be expanded to include immunohistoincompatible donors, while at the same providing data on potential-organ-donors that a given recipient should avoid.

The dosage of the anti-HLA-antibody-depleting agent or the transplant-treatment composition administered will be an immunosuppressive effective amount of active ingredient(s) and will, of course, vary depending upon known factors such as the pharmacodynamic characteristics of the particular active ingredient, its mode and route of administration; the age, health, and weight of the recipient; nature and extent of symptoms; kind(s) of concurrent treatment, frequency of treatment, the effect desired, and the like. Treatment suitable to substantially reduce the level of anti-HLA antibodies usually require a dosage of the active ingredient in the range of about 0.1 to 1000 milligrams per kilogram of body weight. Ordinarily 1 to 500, and preferably 0.1 to 100 milligrams per kilogram per dose is effective to obtain desired results.

In a preferred embodiment, potential transplant recipients who display predictors of asymptomatic rejection (i.e., dramatic increase in IL-2 levels and positive crossmatch with the transplant specimen) can be treated with in the range of about 1–10 cc/kg of a 5–10% (with 10% being presently preferred) aqueous solution of anti-HLA-antibody-depleting agent 1–3 times per week for 2–6 weeks.

Methods of administering the anti-HLA-antibody-depleting-agent or the transplant-treatment composition of the invention are well-known in the art. The immunosuppressive compositions (active ingredients) described herein can be administered in a variety of ways, i.e., by any means that produces contact of the active ingredient(s) with the agent's site of action in the body of a mammal. The administration can be by any conventional means available for use in conjunction with pharmaceuticals, preferably by intravenous injection; either as individual therapeutically active ingredients or in a combination with other therapeutically active ingredients. They can be administered alone, but are generally administered with a pharmaceutical carrier selected on the basis of the chosen route of administration and standard pharmaceutical practice.

As used herein, the term "allograft" or "graft" refers to a collection/assemblage of cells that is derived from a source other than the transplant-recipient, i.e., the cells are heterologous. The allograft is selected so as to provide the graft-recipient with a necessary physiological function in the body. Typically, the cells of the graft are organized in the form of a critical body organ. A variety of allografts suitable for use in the present invention are well-known in the art, such as bone marrow, kidney, heart, liver, neuronal tissue, lung, pancreas, and the like. Presently preferred, according to the present invention, candidates for heart and kidney transplant procedures are treated.

In one embodiment of the present invention, the transplanted allograft is a kidney. Potential kidney transplant recipients are typically on dialysis treatment, which can be for a period of a few years or more. These patients are therefore "highly sensitized" and readily amenable to screening with a variety of histocompatibility assays that are routinely employed to assess the presence of preformed anti-HLA antibodies in the potential organ-recipient that are reactive with an HLA antigen of a potential organ-donor.

In another embodiment of the present invention, the transplanted allograft is an organ whose cold ischemia time is very short, such as a heart. The risk involved in transplanting a heart is substantially higher than with many other organs, e.g., a kidney. For example, the heart transplant candidate risks dying on the waiting list while waiting for a prospectively matched compatible organ. In addition, a heart transplant donor is typically identified within hours before the actual transplantation is to take place, and there is insufficient time to perform the crossmatch assays that are generally employed to screen for graft/host histocompatibility. Heart transplant candidates are thus at risk of undergoing a hyperacute rejection from an incompatible organ crossmatched retrospectively.

If a kidney is rejected, the patient can be returned to dialysis treatment. In contrast, if a heart is rejected, no alternative remedy is available to the patient, and the rejection of the heart allograft is likely to result in the death of the patient. Because no alternate course of treatment is available, physicians are highly selective in choosing potential heart transplant donors. In view of the heightened scrutiny involved in transplanting a heart, the invention method of increasing the likelihood of a negative crossmatch dramatically increases the pool of heart organs that the patient will not reject and therefore provides the patient with an increased likelihood of survival.

As used herein, "transplant" or various grammatical forms thereof, means the physical act of providing a patient with an allograft. The transplant can be either a primary graft or a regraft. Methods for conducting the transplantation procedures for a variety of body organs are well-known in the art. See, for example, Danovitch, G., *Handbook of Kidney Transplantation,* Little Brown & Co., Boston, Mass. 1992.

Patients contemplated for application of the invention methods are mammals including: humans, domesticated animals, and primates. Typically, patients in need of a transplantation procedure are those who have a higher than normal level of anti-HLA antibodies that are reactive against foreign tissue. Most of these patients, typically, will have been exposed to blood products (i.e., dialysis patients), or will have experienced pregnancy. Such patients are referred to herein as "sensitized".

The term "crossmatch" refers to assays that determine the presence of anti-HLA antibodies in a candidate transplant patient that are reactive with the HLA antigen on the cells of a another individual (i.e., a potential organ-donor). A "positive" crossmatch, or reference to a "histoincompatible" organ, refers to the presence of anti-HLA antibodies that are immunoreactive with the HLA-antigen on the cells of the potential organ-donor, such that transplantation of an allograft from a donor with a positive crossmatch will frequently result in a hyperacute, acute, or chronic rejection of the allograft, but usually the former. In contrast, "negative" crossmatch refers to the absence of anti-HLA antibodies that are immunoreactive with the HLA-antigen on the cells of the potential organ-donor, such that upon transplant of an allograft from a donor the allograft is not likely to be rejected.

Higher than normal levels of anti-HLA antibodies in a potential transplant patient can be determined by a variety of methods well-known in the art. See, for example, screening for percent panel reactive antibodies (PRA), described hereinafter in the General Methods Section.

A patient displaying greater than about 50% PRA is said to be "highly" sensitized. PRA refers to the percentage of individuals in an HLA typed panel (i.e., potential organ-donors) with which blood serum from a given patient will immunoreact. For example, a patient's serum that reacts with (i.e., is cytotoxic to) positive lymphocytes from 95 of 100 individuals is said to have a PRA value of 95%.

The invention methods allow the level of anti-HLA antibodies subclasses to be substantially reduced, i.e., to be reduced sufficiently to allow antibody definition. In addition, the substantial reduction of anti-HLA antibodies is sufficient to allow, or increase the likelihood of, negative crossmatch between host tissue and donor tissue. Preferably, the "substantial reduction in the level of anti-HLA antibodies (subclasses)" in a given patient, as determined by the mean PRA value, is by at least 20%, preferably 50%, more preferably 80%; with reductions of 100% especially preferred.

In accordance with another embodiment of the present invention, there is provided a method for reducing the amount of anti-HLA-alloantibodies in a transplant candidate (thereby rendering the candidate transplant patient less susceptible to rejection of an allograft), said method comprising administering to said candidate, prior to transplantation, an anti-HLA antibody reducing amount of an anti-HLA-antibody-depleting-agent.

In accordance with yet another embodiment of the present invention, there is provided a method for decreasing the host versus graft response (i.e., rejection) in a transplant patient (thereby increasing the acceptance of allograft by the transplant recipient and/or increasing the life of allograft in the transplant recipient), said method comprising administering to said patient an anti-HLA antibody reducing amount of an anti-HLA-antibody-depleting-agent, and optionally a chemical immunosuppressive agent.

When combination treatment (i.e., dual administration of anti-HLA-antibody-depleting-agent and chemical immunosuppressive agent) is employed, dosage levels for the anti-HLA-antibody-depleting-agent are comparable to levels presented above. Dosage levels for chemical immunosuppressive agent typically fall in the range of about 1 to 1000 milligrams per kilogram of body weight. Ordinarily, 5 to 750 and preferable 10–500 milligrams per kilograms per dose is effective to obtain desired results. Modes of administration as described above are suitable for administration of chemical immunosuppressive agent.

Exemplary chemical immunosuppressive agents contemplated for use in the practice of the present invention are well-known in the art. Suitable immunosuppressive agents include, for example, Cytoxan (cyclophosphamide) azathioprine (AZA), corticosteroids (such as prednisone), OKT3, FK506, mycophenolic acid or the morpholinethylester thereof, 15-deoxyspergualin, rapamycin, mizoribine, misoprostol, anti-interluekin-1 (IL-2) receptor antibodies, anti-lymphocyte globin (ALG), and the like.

In a presently preferred embodiment of the invention, the transplant-treatment composition (when employed post-transplant) contains IVIg and Cytoxan.

In accordance with another embodiment of the present invention, there is provided a pre-transplant assay for predicting which patients are amenable to treatment with the invention methods of transplantation. The pre-transplant assay also allows the determination of one or more residual anti-HLA antibody specificities in the transplant candidate, which thus permits the determination and avoidance of a specifically defined population of unsuitable donor-organs for transplant.

The invention will now be described in greater detail by reference to the following non-limiting examples.

General Methods

For the experimental techniques employed herein, see ASHI Laboratory Manual, 2 ed., Zachary & Teresi, American Society Histocompatibility and Immunogenetics, Lenexa, Kans., incorporated herein by reference.

pH adjustment of IVIg and glycine.

Low pH is known to have a detrimental effect on lymphocyte viability. In order to perform the inhibition assays which use a lymphocytotoxic assay, the pH of both the IVIg and glycine (pH 4.25) were adjusted to neutral using 1M Tris-HCl (pH 8.0), prior to being used to dilute the sera. This resulted in a 1:12 dilution of the IVIg or glycine and maintained the Ig in solution.

PRA Assay

To ascertain panel reactive antibody (PRA), patient sera were tested in a microlymphocytoxic assay on an HLA typed lymphocyte panel of 50 individuals. Cells were stained with C-FDA (1:150 dilution of 10 mg/ml stock in 1× PBS, 15 min. at 37° C.), washed and dispensed (1 ml/well at $2\times10^6$ cells/mil) into oiled Terasaki trays containing 1 $\mu$l of patient serum/well. Cells were incubated with serum for 30 min. at 21° C., at which time 5 $\mu$l prescreened rabbit complement (Gen-Trak) was added to each well and the incubation continued for 3 hrs at 21° C. for peripheral blood lymphocytes (PBLs) or 2 hrs for T cells isolated on Dynabeads (HLA Cell Prep I, Dynal, Great Neck, N.Y.).

Crossmatch Assay

Crossmatches were performed using donor spleen or lymph node cells. T cell crossmatches (TXM) were performed after depleting the donor cells of B cells by selection on Dynabeads (HLA Cell Prep II) ×2, and then positively selecting the T cells with Cell Prep I. B cell crossmatches were performed after depleting the donor cells of T cells by selection on Dynabeads (CD2) XI and then positively selecting the B cells with Cell Prep II. The incubation with serum for TXM was 30 min. at 21° C., followed by a 2 hr. complement incubation. The incubation with serum for the BXM was 30 min. at 37° C., followed by a 2 hr. complement incubation at 21° C. Dead cells were visualized using 0.1% ethidium bromide and read using darkfield fluorescence microscopy. Cell viability in the negative control exceeded 90% in all cases and scoring was based on the standard HLA scoring of 1=0–10%, 2=11–20%, 4=21–50%, 6=51–80%, 8=81–100% kill over background. For DTT, TXM or BXM, the same protocols were used except that the sera were first treated for 30 min. at 37° C. with a 1/10 volume of 0.05M DTT, prior to plating into the wells. All sera were tested in doubling dilutions (neat to 1:4), and all assays were performed in triplicate.

In vitro inhibition of sera with IVIg.

Individual sera from HLA sensitized patients or HLA typing sera were diluted in an equal volume of neutral pH glycine (0.2M, Sigma) or IVIg (10% Gamimune N, Cutter/Miles) and dispensed in one $\mu$l aliquots in duplicate into 72 well oiled Terasaki trays. For titrations, doubling dilutions of the sera were first made in prescreened normal human serum (untransfused male, type AB), and then each dilution diluted with an equal volume of glycine or IVIg to maintain constant serum: IVIg proportions. DTT treatment was as described above. Plates were used immediately or after being frozen at −70° C. Cells were prepared as for the modified microlymphocytoxicity assay described above for ascertainment of PRA. Cells were incubated with glycine or IVIg treated sera for 30 min. at 21° C. followed by a complement (Prescreened rabbit complement, Gen-Trak) incubation at 21° C. for 3 hrs for PBLs or 2 hrs for T cells isolated on Dynabeads (HLA Cell Prep I). Inhibition was determined by comparing the IVIg treated serum to the same serum diluted in glycine. Inhibition was considered to have occurred when the glycine treated serum gave duplicate scores of 4+ or greater while the same serum treated with IVIg gave duplicate scores of 1 or 2+.

Soluble HLA assay

Soluble HLA content of IVIg was determined using the SangStat Medical sHLA-STAT Class I ELISA assay, according to the supplier's directions, except that a 2-fold additional doubling dilution of the lowest suggested standard dilution was included to extend the range of the standard (1.55–125 ng/ml). IVIg was brought to neutral pH as described above prior to assay to avoid detaching the capture antibody coated to the plate. IVIg was run at 1:1, 1:2, 1:5 and 1:25 dilutions in duplicate, since the 1:1 concentration can be inhibitory in this assay.

In the final fractionation assays, which were the most reliable, the initial incubation of IVIg with the antibody coated wells was 90 mins at 21° C. followed by a 30 min incubation at 21° C. with anti-$\beta_2$ microglobulin/horseradish peroxidase conjugate. $OD_{490}$ readings were performed using a UV Max kinetic microplate reader (Molecular Devices).

Fractionation Assay

To separate all the IgG subclasses from soluble antigen and/or other immunoglobulin isotypes, the Acti-Disk separation and Purification Cartridge, recombinant protein G activated, ultra high capacity (100–125 mg IgG) (FMC) was used. This size cartridge was selected in order to have sufficient material after fractionation in both the eluate and effluent to test against the various panels and to perform ODs and soluble antigen assays. It was considered important to have all of the IgG on a single filter rather than eluting it from several smaller capacity filters and chance losing activity due to artifactual loss on the filter. The protein G cartridge was used after first diluting the IVIg 1:10 in glycine, adjusting the pH to 7.0, and passing the material through a $0.2\mu$ Millex GS (Millipore) filter. The cartridge was primed according to the supplier's directions using a peristaltic pump, the first 5 ml discarded, and then the sample loaded and recirculated for 30 mins at 5.5 ml/min. The effluent was collected and the column washed. The IgG was then eluted from the cartridge in 5 ml fractions, the pH of each fraction adjusted with 2M Tris to neutral, and the fractions combined. The effluent and eluate were then separately concentrated 1OX using Centriprep 10 concentrators (Amicon) according to the manufacturer's directions.

EXAMPLES

Sera from eighteen patients awaiting transplant (15 kidney, 2 liver, 1 heart) with PRAs ranging from 40–100% (mean: 90%) were diluted 1:2 in either 10% IVIg or 0.2M glycine (IVIg carrier) to obtain the maximum possible concentration of IVIg (5%) and serum. In some sera there was a dilution effect seen (FIG. 1), but the PRAs in the glycine treated sera still ranged from 40–100% (mean: 77%). By contrast, IVIg treated sera had a mean reduction in absolute PRA of 35% (range: 4–70%; inhibition 4–100%), with residual PRAs ranging from 0–96% when compared to the glycine control. Early experiments in which 5% IVIg (2.5% effective concentration with serum) was used to inhibit patient sera in vitro showed a less impressive reduction in PRA, suggesting that the limiting factor is the effective concentration of IVIg which can be obtained in vitro. All data presented herein were obtained using the 10% IVIg preparation.

TABLE 1

| PATIENT # | NEAT PRA | GLYCINE | IVIg | HLA ANTIGEN SPECIFICITY |
|---|---|---|---|---|
| 1 | 72 | 58 | 28 | 1/4 25;3/9 26;2/2 34;1/2 74;1X |
| 2 | 92 | 96 | 62 | 21/23 A2;OX |
| 3 | 98 | 90 | 50 | |
| 4 | 100 | 100 | 96 | |
| 5 | 100 | 100 | 30 | |
| 6 | 100 | 48 | 16 | Weak |
| 7 | 94 | 92 | 80 | |
| 8 | 86 | 68 | 38 | 5/8 A1;12/23 A2;1/3 68;2X |
| 9 | 92 | 90 | 32 | 12/23 A2;2/4 A28;3X |
| 10 | 92 | 62 | 46 | Much Weaker |
| 11 | 92 | 88 | 54 | 13/23 A2;10/12 24;2/2 23;1/2 9.3;5X |
| 12 | 78 | 44 | 0 | (α16+) |
| 13 | 98 | 42 | 6 | Weak |

TABLE 1-continued

| PATIENT # | NEAT PRA | GLYCINE | IVIg | HLA ANTIGEN SPECIFICITY |
|---|---|---|---|---|
| 14 | 90 | 74 | 30 | |
| 15 | 100 | 98 | 82 | |
| 16 | 96 | 100 | 44 | 15/23 A2;3/3 29;3/4 28;1/3 68;1/4 69;1X |
| 17 | 96 | 90 | 52 | 5/8 A1;18/23 A2;1/3 68;1/4 69;1X |
| 18 | 40 | 38 | 0 | 23/23 A2 |

In 7/18 sera tested (72–96% PRA untreated), the residual HLA antibody specificity could be determined after IVIg treatment (Table 1). In addition, a striking feature of five of these was that they had residual anti-A2 activity but reacted with only half of the HLA-A2+panel cells. However, the pattern of reactivity with the entire A2 panel was distinct for each of these five sera with seven apparent "groups" of A2 (Table 2).

TABLE 2

RESIDUAL HLA-A2 ACTIVITY
OF HIGH PRA (86–96%) SERA TREATED WITH IVIg

| PANEL CELL ID # | PATIENT # | | | | |
|---|---|---|---|---|---|
| | 17 | 16 | 9 | 8 | 11 |
| 1 | + | + | + | + | + |
| 2 | + | + | + | + | + |
| 3[1] | + | + | + | + | + |
| 4[1] | + | + | + | + | + |
| 5 | + | + | + | + | |
| 6 | + | + | + | + | |
| 7 | + | + | + | + | |
| 8 | + | + | + | | + |
| 9[1] | + | + | + | | + |
| 10[1] | + | + | | | + |
| 11 | + | + | | + | + |
| 12[1] | + | | + | + | + |
| 13 | + | | + | + | + |
| 14[2] | + | + | | | |
| 15 | + | + | | | |
| 16 | + | + | | | |
| 17[1] | | | | + | + |
| 18 | | | | | |
| 19[1] | | | | | + |
| 20 | + | | | | |
| 21 | | | | | |
| 22[1] | | | + | | |
| 23 | | | | | |

[1]A*0201
[2]A*0205

Class I oligotyping of DNA from each "group" was performed by using PCR-SSOP (See Fernandez-Vina et al., Human Immunol., 33:163 (1992). The results (Table 2) show that the patterns of reactivity are not due to differences in A2 subtype since 9/10 cells tested representing each "group" typed as A*0201.

Since certain HLA specificities were not inhibited by IVIg in these 19 patient sera, the ability of IVIg to inhibit exceptionally well characterized reagent grade HLA alloantisera covering an array of HLA-A and B locus specifities used on our local typing trays (n=21; Table 3) was assessed to determine whether any consistent features were present in the sera which could not be inhibited. The ability of IVIg to inhibit the cytotoxic reactivity of these sera varied and could be characterized as complete (n=7); partial (i.e., incomplete, with inhibition for some but not all cells with a particular antigen; n=3); differential (i.e., complete for one or more specificities, no inhibition for another; n=8); or absent (n=3). To determine whether these patterns of inhibition were a function of titer, sera treated with glycine or IVIg were titered past their end points (see General Methods). Similar studies were performed on the patient sera discussed above showing residual A2 activity and a differential pattern after IVIg treatment. The results for the typing sera and ⅔ patient sera are shown in Table 3 together with the reduction in doubling dilutions for each specificity.

TABLE 3

In Vitro Inhibition of Patient and HLA Typing Sera by IVIg

| HLA TYPING SERA | | INVERSE OF DILUTION TREATMENT | | INHIBITION (LOG$_2$ DILUTION) |
|---|---|---|---|---|
| SERUM | SPECIFICITY | GLYCINE | IVIg | |
| HARB | A2 | >16 | 4 | 2 |
|  | A69 | >16 | 4 | 2 |
|  | A68 | 4 | 2 | 1 |
| MOOR | A2 | 4 | 0 | >2 |
| VARG | A2 | 8 | 2 | 2 |
| BROW | A25 | 4 | 0 | >2 |
|  | A26 | 8 | 4 | 1 |
|  | A34 | 4 | ≤1 | ≥2 |
| DEGE | A25 | >16 | 1 | 4 |
|  | A26 | >16 | 4 | 2 |
|  | A34 | >16 | ≤1 | ≥4 |
| TERR | A26 | 4 | 1 | 2 |
| HOLL | A25 | 4 | 0 | >2 |
|  | A26 | 4 | 2 | 1 |
|  | A34 | 2 | 2 | 0 |
|  | A29 | NT | NT | — |
|  | A31 | 4 | 2 | 1 |
|  | A32 | 4 | 4 | 0 |
|  | A33 | 2 | 2 | 0 |
|  | A74 | NT | NT | — |
| HOLD | B51 | >16 | 4 | 2 |
|  | B52 | >16 | 4 | 2 |
|  | B59 | >16 | 0 | >4 |
| WALL | B51 | 2 | 0 | >1 |
|  | B52 | 2 | 2 | 0 |
|  | B59 | 2 | 0 | >1 |
| CRIS | B35 | 2 | 0 | >1 |
|  | B51 | 2 | 0 | >1 |
| FREC | B7 | 2 | 2 | 0 |
| KANN | B7 | 2 | ≤1 | ≥1 |
| WESE | B7 | 4 | ≤1 | ≥2 |
| KOEL | B8 | 8 | 4 | 1 |
|  | B59 | 8 | 0 | >3 |
| MARS | B8 | 2 | 0 | >1 |
| BLAC | B57 | 8 | 4 | 1 |
|  | B62 | 8 | 4 | 1 |
| VERM | A1 | 2 | 1 | 1 |
|  | B62 | 2 | 0 | >1 |
| REEV | A2 | 8 | 4 | 1 |
|  | B57 | 16 | 4 | 2 |
| RATL | B57 | 8 | 0 | >3 |
|  | B62 | 8 | 0 | >3 |
| McCA | B55 | 4 | 4 | 0 |
| WOOD | B7 | 8 | 8 | 0 |
|  | B55 | 8 | 0 | >3 |

TABLE 3-continued

In Vitro Inhibition of Patient and HLA Typing Sera by IVIg

| HLA TYPING SERA | | INVERSE OF DILUTION TREATMENT | | INHIBITION (LOG$_2$ DILUTION) |
|---|---|---|---|---|
| SERUM | SPECIFICITY | GLYCINE | IVIg | |
| PATIENT SERA | | | | |
| KI | A2 | 8 | 0–2 | 2–4 |
|  | B8 | 255 | 64–128 | 1–2 |
| ME | A2 | 32 | 0–2 | 4–6 |
|  | B51 | 128 | 64 | 1 |

In the case of serum Ratliff (B57, 62), IVIg was able to completely inhibit both specificities which each have titers of 1:8, while in serum Black (same specificities, same titer), IVIg was only able to reduce the titer to 1:4. These results together with those from sera recognizing B7, for example, confirm that the patterns of inhibition are independent of specificity. Moreover, results from the patient sera (KI, ME) show that, while one specificity has a much higher titer than the other, the same degree of inhibition as measured by drop in titer is not seen for both specificities. Results with sera Holden and Koelsch also confirm that in typing sera with reasonably high titer, the titer does not account for the differential inhibition seen.

In vivo efficacy was then studied for two HLA sensitized patients awaiting transplantation for whom in vitro testing had demonstrated a significant inhibitory effect of IVIg. The first patient (KI; 13 yr old) was highly sensitized (95% PRA) awaiting a second kidney transplant. In vivo administration of IVIg resulted in the progressive reduction of his PRA over a four week period until it reached a plateau of 15% due to residual A2, B8 antibody (Tables 1, 2 and 3). He was successfully transplanted two years later (donor HLA-antigen specifities: A29, 30; B44, 70; Cw2, 4; DR1, 2) and remains rejection free nine months post transplant.

The second patient awaiting heart transplantation (PRA 40%), had a strong IgG antibody to HLA-A2; [A28]: A68, A69; [B17]: B57, B58. In vivo administration of IVIg beginning two months pretransplant also resulted in the progressive decline of her HLA antibody, with the crossreacting specificities (i.e., A28, B17) disappearing first, and the A2 reactivity disappearing more gradually (Table 4). Remarkably, when the patient's serum was tested with and without DTT at intervals after IVIg infusion, an early and significant inhibition of PRA was seen in the untreated (no DTT) serum, while a much more gradual loss of PRA was seen in the DTT treated sample. On the date of transplant, there was virtual absence of any reactivity against the previously positive panel (1/16) in the patient's untreated serum, but residual IgG activity (10/16) in the DTT treated specimen against this same panel. Crossmatch results for donor T and B cells are shown in Table 5.

TABLE 4

Effect of IVIG treatment in vivo on cytotoxic reactivity of sera from heart transplant recipient against original positive panel.

| | | <-- PRE-IVIG --> | | | | <-------------IVIG TX PERIOD-----------------> | | | | | | | | TXP | | <-- POST-TXP IVIG ---> | | | | |
|---|---|---|---|---|---|---|---|---|---|---|---|---|---|---|---|---|---|---|---|---|
| | DATE: | 5-13-92 | | 6-1-92 | | 11-6-92 | | 11-17-92 | | 12-2-92 | | 12-16-92 | | 12-30-92 | | 1-4-92 | | 2-1-93 | | 2-15-93 | | 3-3-93 | |
| PANEL PHENOTYPE | DTT TX: | − | + | − | + | − | + | − | + | − | + | − | + | − | + | − | + | − | + | − | + | − | + |
| A2,24;B35,51;Cw4,− | | 8 | 8 | 8 | 8 | 6 | 8 | 4 | 8 | 1 | 8 | 4 | 8 | 1 | 8 | 1 | 8 | 8 | 8 | 1 | 4 | 1 | 1 |
| A2,32;B7,35;Cw4,7 | | 8 | 8 | 8 | 8 | 8 | 8 | 6 | 8 | 4 | 8 | 4 | 8 | 1 | 8 | 1 | 8 | 1 | 2 | 1 | 1 | 1 | 1 |
| A2,−;B37,51;Cw6,− | | 8 | 8 | 8 | 8 | 8 | 8 | 8 | 8 | 8 | 8 | 8 | 8 | 1 | 8 | 8 | 8 | 8 | 8 | 4 | 6 | 1 | 1 |
| A2,28;B8,51;Cw7,− | | 8 | 8 | 8 | 8 | 6 | 8 | 6 | 8 | 1 | 8 | 1 | 8 | 1 | 6 | 1 | 1 | 8 | 8 | 1 | 1 | 1 | 1 |
| A2,24;B27,44;Cw5,6 | | 8 | 8 | 8 | 8 | 8 | 8 | 6 | 8 | 1 | 8 | 6 | 8 | 1 | 8 | 1 | 8 | 1 | 6 | 1 | 1 | 1 | 1 |
| A2,3;B7,35;Cw4,7 | | 8 | 8 | 8 | 8 | 6 | 8 | 2 | 8 | 1 | 8 | 1 | 8 | 1 | 8 | 1 | 8 | 1 | 1 | 1 | 1 | 1 | 1 |
| A2,34;B35,58;Cw4,6 | | 8 | 8 | 8 | 8 | 6 | 8 | 4 | 8 | 1 | 8 | 8 | 8 | 4 | 8 | 1 | 8 | 8 | 8 | 1 | 1 | 1 | 1 |
| A2,−;B38;61;Cw3,7 | | 8 | 8 | 8 | 8 | 6 | 8 | 4 | 8 | 1 | 8 | 8 | 8 | 1 | 6 | 1 | 4 | 1 | 1 | 1 | 1 | 1 | 1 |
| A2,24;B7,18;Cw5,7 | | 8 | 8 | 8 | 8 | 4 | 8 | 1 | 8 | 1 | 8 | 4 | 8 | 1 | 8 | 1 | 8 | 1 | 1 | 1 | 1 | 1 | 1 |
| A2,2;B13,62;Cw3,6 | | 6 | 8 | 6 | 8 | 4 | 8 | 1 | 6 | 1 | 6 | 1 | 8 | 1 | 8 | 1 | 8 | 2 | 4 | 1 | 1 | 1 | 1 |
| A23,68;B13,52;Cw6,− | | 1 | 8 | 1 | 8 | 1 | 6 | 1 | 1 | 1 | 1 | 1 | 1 | 1 | 1 | 1 | 1 | 8 | 8 | 8 | 8 | 1 | 2 |
| A26,69;B13,55;Cw1,7 | | 1 | 8 | 1 | 8 | 1 | 6 | 1 | 4 | 1 | 1 | 1 | 6 | 1 | 1 | 1 | 1 | 1 | 1 | 1 | 1 | 1 | 1 |
| A1,69;B55,57;Cw1,6 | | 8 | 8 | 8 | 8 | 1 | 8 | 1 | 8 | 1 | 8 | 1 | 8 | 1 | 6 | 1 | 4 | 8 | 8 | 1 | 1 | 1 | 1 |
| A1,24;B35,57;Cw4,6 | | 4 | 8 | 1 | 8 | 1 | 6 | 1 | 1 | 1 | 1 | 1 | 1 | 1 | 1 | 1 | 1 | 8 | 8 | 2 | 6 | 1 | 1 |
| A1,−;B57,63;Cw6,− | | 4 | 8 | 1 | 8 | 1 | 6 | 1 | 1 | 1 | 1 | 1 | 1 | 1 | 1 | 1 | 1 | 8 | 8 | 4 | 8 | 1 | 1 |

TABLE 5

Crossmatch Results of Sera from heart transplant recipient collected before and after transplant

| | TXM | | | DTT TXM | | | BXM | | | DTT BXM | | |
|---|---|---|---|---|---|---|---|---|---|---|---|---|
| SERUM DATE | 1:1 | 1:2 | 1:4 | 1:1 | 1:2 | 1:4 | 1:1 | 1:2 | 1:4 | 1:1 | 1:2 | 1:4 |
| 5-13-92 | 8 | 4 | 1 | 8 | 1 | 1 | 8 | 6 | 1 | 8 | 4 | 1 |
| 1-4-93[a] | 1 | 1 | 1 | 1 | 1 | 1 | 1 | 1 | 1 | 1 | 1 | 1 |
| 1-25-93 | 8 | 8 | 8 | 8 | 8 | 8 | 8 | 8 | 8 | 8 | 8 | 8 |
| 2-1-93 | 1 | 1 | 2 | 4 | 2 | 1 | 1 | 1 | 1 | 1 | 1 | 1 |
| 2-15-93 | 1 | 1 | 1 | 1 | 1 | 1 | 1 | 1 | 1 | 1 | 1 | 1 |

[a]Transplant date
TXM = T cell crossmatch with untreated serum.
DTT TXM = T cell crossmatch with DTT treated serum.
BXM = B cell crossmatch with untreated serum.
DTT BXM = B cell crossmatch with DTT treated serum.

For the final crossmatch, the historical serum gives a strongly incompatible crossmatch at all dilutions, while the current serum is completely negative under the same conditions. Three weeks after transplant when the patient returned for a routine biopsy, a new serum specimen was obtained and recrossmatched against her donor. At this time, both the T and B cell crossmatches were strongly incompatible. Although the patient had no signs of rejection on the biopsy, she had elevated IL-2 levels, and another course of IVIg treatment was started. Two weeks later, the TXM had returned to negative with the donor, and the IL-2 levels had returned to normal. The patient remains rejection free four months post transplant.

Studies were performed to determine which fraction of IVIg is responsible for the demonstrated inhibition. Soluble HLA antigen, IgG, IgM and/or IgA were considered as possible mediators, especially in view of the differential inhibition seen with HLA typing reagents and the untreated vs. DTT treated sera from the heart recipient.

Quantitation of the immunoglobulins present in the IVIg was performed and compared to the levels present in normal human serum (NHS). The results indicate that IVIg contains an 8-fold increase of IgG, a 17.5 fold decrease in IgA, and an 11-fold decrease in IgM when compared to NHS.

Fractionation studies were performed as described in the General Methods section. The selection of filters was considered critical to the experimental design, since it was important not to retain soluble antigen, IgM or IgA on any filter, while retaining all subclasses of IgG on the final filter. For this reason, recombinant protein G activated Acti-Disk filter was chosen. This filter retains all subclasses if IgG but no other Ig isotype, instead of the protein A activated Acti-Disk which retains $IgG_{1,2,4}$ as well as IgM, IgA and IgE, but not $IgG_3$. Since use of the Acti-Disk cartridges requires dilution of the IVIg 1:10 prior to filtration, studies were performed to demonstrate that IVIg could be successfully diluted and reconcentrated without loss of activity. Initial studies using Centriprep 30 filters showed that, despite the theoretical suitability of this size cutoff, activity was lost after dilution and reconcentration. Similar studies using Centriprep 10 cartridges showed no loss of inhibitory capability after dilution of IVIg 1:10 and reconcentration to 1:1, when compared to the IVIg used directly without manipulation, and therefore these were selected.

Soluble antigen quantitation was performed on different lots of IVIg using the SangStat soluble antigen kit, with two additional doubling dilutions of the standard to quantitate very low levels. Preliminary results indicated that the standard could be reliably diluted to the equivalent of 1.55 ng/ml before reaching background levels. It was necessary however to bring the pH of the IVIg to 7.0 using 1M Tris-HCl (pH 8.0) as described in the General Methods section in order to have a reliable assay and maintain the Ig in solution. Soluble antigen ranged from not detectable to 9.2 ng/ml, depending on the lot of IVIg assayed and the conditions used.

Figure 2:
FIG. 2 shows the inhibitory activity of fractions of IVIg passed over an ultra high capacity protein G activated Acti-Disk cartridge and tested against lymphocytes from a panel of 8 previously positive cells. Cont=original IVIg as supplied (10%), Recon=IVIg diluted 1:10 and concentrated 10×; Effluent=flow through from protein G column, concentrated 10×; Eluate=fraction eluted from protein G column, concentrated 10×.

The results of the fractionation study are shown in FIG. 2. Soluble antigen was tested in the original IVIg, after 0.2μ filtration, post reconcentration, and in the effluent and eluate of the protein G filter. The results of these assays were considered to be the most reliable of all the soluble antigen assays performed (i.e., excellent replicates, clear standard curve) and soluble antigen was not detectable in any fraction, including the original product.

In order to track protein, $OD_{280}$ readings were performed on each of the fractions. The effluent and eluate from the protein G cartridge were also tested after reconcentration with and without DTT to determine which fraction retained inhibitory capability, and whether it was DTT sensitive or insensitive (i.e., IgM or IgG, respectively). The results indicate that the protein fractionates as expected and clearly support the conclusion that it is the DTT insensitive IgG fraction eluted from the protein G cartridge which contains the inhibitory component of IVIg. The effluent containing the IgM, IgA, and the theoretic but undetectable soluble antigen components has no inhibitory capacity.

HLA sensitized potential transplant recipients were treated with 10 cc/kg body weight of 10% IVIg 1–3 times per week for 3–5 weeks. One patient who displayed predictors of asymptomatic rejection (i.e., dramatic increase in IL-2 levels and positive crossmatch with the transplant specimen) was given a second course of treatment. Serum panel reactive antibody (PRA) values were determined periodically during the treatment protocol. Results are summarized in Table 6.

TABLE 6

| Patient | Treatment no. | PRA levels, % |
|---|---|---|
| 1 | — | 95 |
|   | 1 |   |
|   | 2 |   |
|   | 3 |   |
|   | 4 | 15 |
| 2 | — | 40 |
|   | 1 | 22 |
|   | 2 | 6 |
|   | 3 | 22 |
|   | 4 | 0 |

*ND = not determined

The above data indicate that the patients' PRA decreased progressively after initiation of treatment. In addition, patient #2 was determined to have a positive T- and B-cell crossmatch with donor prior to the above-described IVIg treatment; while crossmatch after IVIg treatment (and prior to transplant) was negative. Both patients have subsequently been transplanted (patient #1—kidney; patient #2—heart) and neither has experienced rejection.

Figure 3:
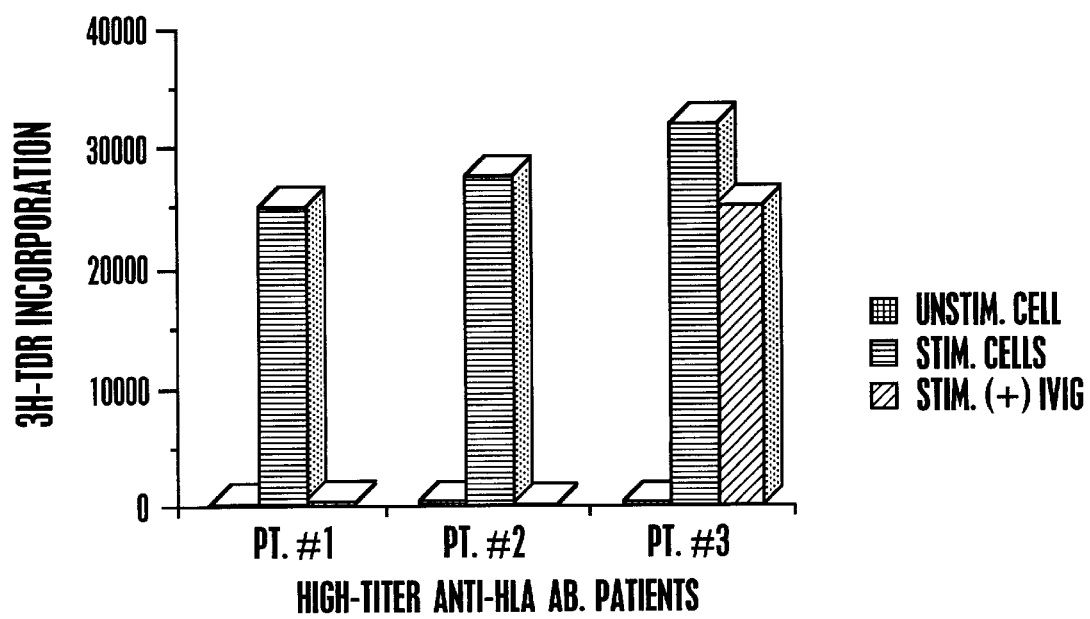
FIG. 3 shows the results of the mixed lymphocyte reaction described the Examples.

The sera from highly sensitized (high anti-HLA antibody) patients who were on dialysis awaiting kidney transplantation were subjected to the mixed lymphocyte culture reaction employing well-known techniques described in ASHI Laboratory Manual, 2ed. supra. The results are shown in FIG. 3 and reveal how IVIg potently inhibits the mixed lymphocyte reaction (an in vitro surrogate for graft rejection) in ⅔ patients tested.

While the invention has been described in detail with reference to certain preferred embodiments thereof, it will be understood that modifications and variations are within the spirit and scope of that which is described and claimed.

That which is claimed is:

1. A method for transplanting a histoincompatible organ allograft into an HLA-sensitized transplant candidate, consisting of
   (I) administering to the transplant candidate prior to transplantation an amount of an anti-HLA antibody depleting agent selected from the group consisting of IVIg and an IgG fraction of IVIg, immunosuppressively effective to substantially
      (a) reduce the serum level of anti-HLA antibodies,
      (b) result in a negative crossmatch of the transplant candidate with potential organ donors relative to the crossmatch attained without the administration of the agent, and
      (c) enhance organ allograft survival in the transplant candidate; and
   (II) transplanting an organ allograft into the transplant candidate.

2. The method of claim 1, wherein the agent is an IgG fraction of IVIg.

3. The method of claim 1, wherein the agent is IVIg.

4. The method of claim 1, where in the agent is administered as a composition comprising about 5 to about 90% agent per dose.

5. The method of claim 1, wherein the immunosuppressively effective amount of agent administered is about 0.1 to about 1000 mg/kg body weight.

6. The method of claim 1, wherein the organ allograft comprises a heart.

7. The method of claim 1, wherein the organ allograft comprises a kidney.

8. The method of claim 5, wherein the immunosuppressively effective amount of the agent administered is about 1 to about 500 mg/kg body weight per dose.

9. The method of claim 1, wherein the serum level of the recipient's anti-HLA antibodies is reduced sufficiently to allow a negative crossmatch between host and donor tissues.

10. The method of claim 1 wherein the organ allograft comprises a lung.

11. The method of claim 5, wherein the agent is administered as a composition comprising about 25 to about 75% anti-HLA antibody depleting agent.

12. The method of claim 11, wherein the agent is administered as a composition comprising greater than about 50% anti-HLA antibody depleting agent.

13. The method of claim 11, wherein the agent is administered as a composition comprising about greater than about 90% anti-HLA antibody depleting agent.

14. The method of claim 11, wherein the agent is administered as a substantially pure preparation.

15. The method of claim 1, wherein the agent is administered about 1 to 3 times per week for a period of time of about 1 to about 6 weeks.

16. The method of claim 5, wherein the agent is administered about 1 to 3 times per week for a period of time of about 1 to about 6 weeks.

17. The method of claim 1, wherein the organ allograft comprises a liver.

18. The method of claim 1, wherein the organ allograft comprises a pancreas.

* * * * *